US008824627B2

(12) United States Patent
Nakanishi (10) Patent No.: US 8,824,627 B2
(45) Date of Patent: Sep. 2, 2014

(54) X-RAY CT SCANNER AND IMAGE PROCESSING APPARATUS

(75) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/584,340

(22) Filed: Aug. 13, 2012

(65) Prior Publication Data

US 2012/0321036 A1     Dec. 20, 2012

Related U.S. Application Data

(63) Continuation of application No. PCT/JP2012/065183, filed on Jun. 14, 2012.

(30) Foreign Application Priority Data

Jun. 15, 2011  (JP) .................................. 2011-133121

(51) Int. Cl.
  *G01N 23/04*  (2006.01)
  *G06K 9/46*  (2006.01)

(52) U.S. Cl.
  USPC ............................................ 378/19; 382/131

(58) Field of Classification Search
  CPC ...................................................... G06T 11/03
  See application file for complete search history.

(56) References Cited

U.S. PATENT DOCUMENTS 5,442,674 A * 8/1995 Picard et al. .................... 378/20
5,706,324 A * 1/1998 Wiesent et al. .................. 378/4
6,466,638 B1 * 10/2002 Silver et al. ...................... 378/4
7,016,456 B2   3/2006 Basu et al.
2005/0047552 A1 * 3/2005 Arai et al. ..................... 378/207
2007/0172025 A1 * 7/2007 Seto ............................... 378/18

FOREIGN PATENT DOCUMENTS

| CN | 1628610 A | 6/2005 |
| CN | 101006930 A | 8/2007 |
| CN | 101750021 A | 6/2010 |
| JP | 60-256436 | 12/1985 |
| JP | 63-125242 | 5/1988 |
| JP | 2005-58758 | 3/2005 |

(Continued)

OTHER PUBLICATIONS

International Search Report issued Sep. 18, 2012, in Patent Application No. PCT/JP2012/065183 (with English translation of Category of Cited Documents).

(Continued)

*Primary Examiner* — Hoon Song
*Assistant Examiner* — Danielle Fox
(74) *Attorney, Agent, or Firm* — Oblon, Spivak, McClelland, Maier & Neustadt, L.L.P.

(57) ABSTRACT

According to one embodiment, an X-ray CT scanner includes a gantry unit, a reconstruction unit, an extraction unit, and an output unit. The gantry unit includes an X-ray source and an X-ray detector and is configured to rotate the source and the detector. The reconstruction unit generates reconstruction image data by using data acquired by the detector. The extraction unit extracts, when using a predetermined phantom as the object, pixel values of pixels existing on a locus surrounding a tomographic image of the phantom contained in reconstruction image data generated by the reconstruction unit based on data acquired by the detector. The output unit outputs an extraction result obtained by the extraction unit or information obtained based on the extraction result.

9 Claims, 6 Drawing Sheets (56) References Cited

FOREIGN PATENT DOCUMENTS

| JP | 2007-202807 | 8/2007 |
|---|---|---|
| JP | 2007-215698 | 8/2007 |
| JP | 2007-222599 | 9/2007 |
| WO | WO 2010/073308 A1 | 7/2010 |

OTHER PUBLICATIONS

International Search Report issued Sep. 18, 2012, in PCT/JP2012/065183 (submitting English translation only).

Chinese Office Action issued Jun. 23, 2014, in China Patent Application No. 201280000721.1 (with English translation).

* cited by examiner

X-RAY CT SCANNER AND IMAGE PROCESSING APPARATUS

CROSS-REFERENCE TO RELATED APPLICATIONS

This application is a Continuation Application of PCT Application No. PCT/JP2012/065183, filed Jun. 14, 2012 and based upon and claiming the benefit of priority from Japanese Patent Application No. 2011-133121, filed Jun. 15, 2011, the entire contents of all of which are incorporated herein by reference.

FIELD

Embodiments described herein relate generally to an X-ray CT (Computed Tomography) scanner which captures a tomographic image by irradiating an object with X-rays and an image processing apparatus which processes the image captured by the X-ray CT scanner.

BACKGROUND

An X-ray CT scanner is configured to reconstruct a tomographic image based on the projection data obtained by causing an X-ray source to irradiate an object with X-rays, while rotating an X-ray source around the body axis of the object, and causing an X-ray detector to detect the X-rays transmitted through the object. The X-ray CT scanner plays an important role in medical activities including disease diagnosis, medical treatment, and surgery planning.

In general, the X-ray CT scanner reconstructs an image, assuming that the locus of an X-ray focus is a true circle. For this reason, the vibration caused when the gantry on which the X-ray source and X-ray detector are mounted rotates becomes the direct cause of a deterioration in the image quality of a reconstructed image, and particularly the spatial resolution.

Conventionally, in consideration of this fact, attempts have been made to suppress vibration by measuring gantry vibration at the time of rotation and adjusting the installed states of the respective units on the gantry so as to reduce the measured value.

As a method of measuring gantry vibration, there is used a method of directly or indirectly measuring the displacement of each mechanism included in the gantry. As a typical method, there is available a method of measuring the displacement of each unit on the gantry while actually rotating the gantry.

However, there are various problems in such a conventional measurement method.

For example, even when a vibration value as a measurement result is very small, if the frequency of the vibration value is high, a noticeable artifact may occur in a reconstructed image. In contrast, even when a vibration value as a measurement result is large, if the frequency of the vibration value is low, the influence of the vibration on image quality may be negligibly small. As described above, the measurement result on gantry vibration and the influence of the vibration on image quality do not always have a one-to-one relationship.

In addition, since it is necessary to measure the vibration values of the respective measurement target portions in various directions, large equipment is required for measurement. Under the circumstances, it is necessary to provide some means for facilitating specifying the degree of influence of gantry vibration on a reconstructed image and the cause of gantry vibration.

DETAILED DESCRIPTION

In general, according to one embodiment, an X-ray CT scanner includes a gantry unit, a reconstruction unit, an extraction unit, and an output unit. The gantry unit includes an X-ray source configured to irradiate an object with X-rays and an X-ray detector configured to detect X-rays transmitted through the object and is configured to rotate the X-ray source and the X-ray detector while placing the X-ray source and the X-ray detector so as to make the X-ray source and the X-ray detector face each other. The reconstruction unit generates reconstruction image data by using data acquired by the X-ray detector. The extraction unit extracts, when using a predetermined phantom as the object, pixel values of pixels existing on a locus surrounding a tomographic image of the phantom contained in reconstruction image data generated by the reconstruction unit based on data acquired by the X-ray detector. The output unit outputs an extraction result obtained by the extraction unit or information obtained based on the extraction result.

Several embodiments will be described with reference to the accompanying drawing. Note that the same reference numerals in the following description denote constituent elements having almost the same functions and arrangements, and a repetitive description will be made only when required.

First Embodiment

Figure 1:
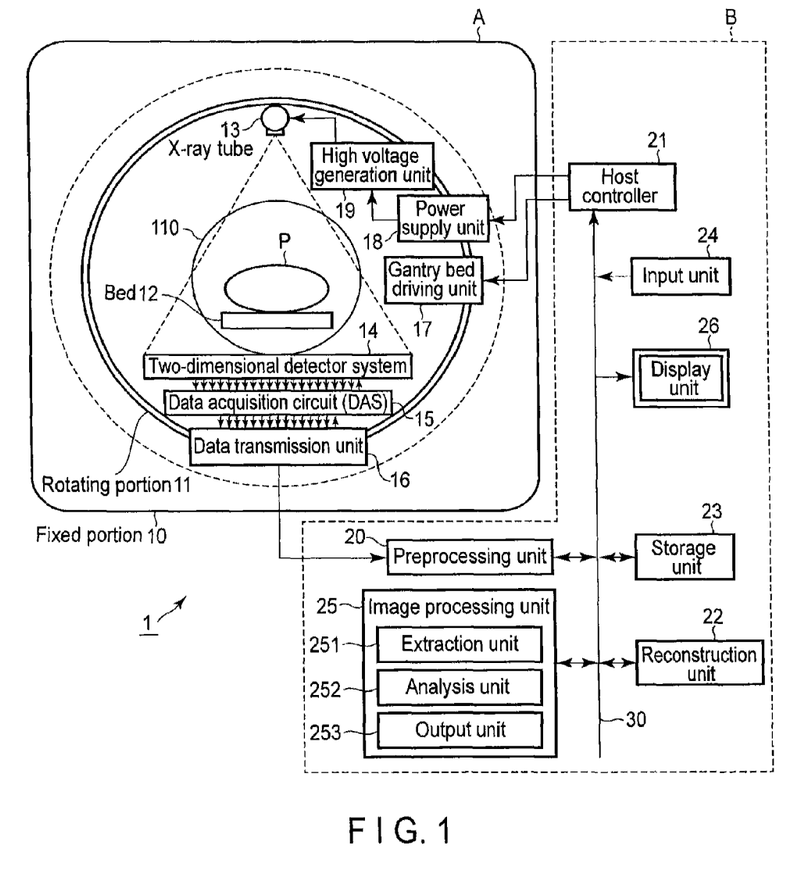
FIG. 1 is a block diagram showing the overall arrangement of an X-ray CT scanner according to the first embodiment.

The first embodiment will be described first.
[Overall Arrangement of X-Ray CT Scanner]
FIG. 1 is a block diagram showing the overall arrangement of an X-ray CT scanner 1 in the first embodiment. As shown in FIG. 1, the X-ray CT scanner 1 is constituted by a gantry apparatus A and a console apparatus B.

The gantry apparatus A acquires projection data (or raw data) by detecting the X-rays applied to and transmitted through an object. Note that the imaging systems of X-ray CT systems include a rotate/rotate type in which an X-ray tube and an X-ray detector system rotate together around an object, and a stationary/rotate type in which many detection elements are arranged in the form of a ring, and only an X-ray tube rotates around an object. The present invention can be applied to either type. In this case, the rotate/rotate type X-ray CT scanner, which is currently the mainstream, will be exemplified.

As shown in FIG. 1, the gantry apparatus A includes a fixed portion 10, a rotating portion 11, a bed 12, an X-ray tube 13, a detector system 14, a data acquisition circuit (DAS) 15, a data transmission unit 16, a gantry bed driving unit 17, a power supply unit 18, and a high voltage generation unit 19.

The X-ray tube 13 is a vacuum tube which generates X-rays, and is provided on the rotating portion 11. The detector system 14 detects the X-rays transmitted through an object P. The detector system 14 is mounted on the rotating portion 11 so as to make the detection surface face the X-ray tube 13.

The rotating portion 11 is provided with an opening portion 110. The bed 12 is disposed in the opening portion 110. The object P is placed on a slide top of the bed 12. The gantry bed driving unit 17 moves the bed 12 in the body axis direction of the object P inserted in the opening portion 110 while rotating the rotating portion 11 around the central axis parallel to the body axis direction. In this manner, the object P is scanned in a wide range.

The data acquisition circuit 15 includes a plurality of data acquisition element rows on which DAS chips are arrayed. The data acquisition circuit 15 receives enormous data (data corresponding to M×N channels per view will be referred to as "raw data") concerning all the channels, i.e., M×N channels, which are detected by the detector system 14. The data acquisition circuit 15 performs amplification processing, A/D conversion processing, and the like for the raw data and collectively transmits the data having undergone these processes to the fixed portion 10 side via the data transmission unit 16 using optical communication.

The fixed portion 10 receives operation power from an external power supply such as a commercial AC power supply. The operation power supplied to the fixed portion 10 is transferred to each unit of the rotating portion 11 via the power supply unit 18 which is, for example, a slip ring.

The high voltage generation unit 19 is constituted by a high voltage transformer, a filament heating converter, a rectifier, a high voltage switch, and the like. The high voltage generation unit 19 converts the operation power supplied from the power supply unit 18 into a high voltage and applies it to the X-ray tube 13.

The console apparatus B will be described next.

The console apparatus B includes a preprocessing unit 20, a host controller 21, a reconstruction unit 22, a storage unit 23, an input unit 24, an image processing unit 25, a display unit 26, and a data/control bus 30.

The preprocessing unit 20 receives raw data from the data acquisition circuit 15 via the data transmission unit 16, and executes sensitivity correction and X-ray intensity correction for the data. Note that the raw data preprocessed by the preprocessing unit 20 will be referred to as "projection data".

The host controller 21 performs comprehensive control concerning various types of processing such as imaging processing, data processing, and image processing.

The reconstruction unit 22 generates reconstruction image data corresponding to a predetermined slice by performing reconstruction processing for projection data based on predetermined reconstruction parameters (a reconstruction region size, a reconstruction matrix size, a threshold for the extraction of a region of interest, and the like).

The storage unit 23 stores various kinds of data such as acquired raw data, projection data, and reconstruction image data.

The input unit 24 includes a keyboard, various kinds of switches, and a mouse, and is used to, for example, input various kinds of scan conditions such as a slice thickness and the number of slices.

The image processing unit 25 performs image processing for display such as window conversion and RGB processing for the reconstruction image data generated by the reconstruction unit 22, and outputs the resultant data to the display unit 26. The image processing unit 25 generates the image data of pseudo three-dimensional images such as a tomographic image of an arbitrary slice, a projection image from an arbitrary direction, and a three-dimensional surface image based on instructions from the operator, and outputs the data to the display unit 26. The display unit 26 displays the output image data as an X-ray CT image.

The data/control bus 30 includes signal lines for connecting the respective units to each other and transmitting/receiving various kinds of data, control signals, address information, and the like.

Note that the image processing unit 25 functions as an image processing apparatus in this embodiment. The image processing unit 25 implements functions as an extraction unit 251, an analysis unit 252, and an output unit 253 by causing a processor to execute computer programs stored in a predetermined memory. The operation of each of the units 251 to 253 will be described later with reference to FIG. 3.

[Artifact by Gantry Vibration]

An artifact due to the vibration of the gantry apparatus A (to be referred to as gantry vibration hereinafter) upon rotation of the rotating portion 11 or operation of the bed 12 can occur in the reconstructed image generated when the X-ray CT scanner 1 having the above arrangement scans an object. Such an artifact will be described with reference to FIG. 2.

Figure 2:
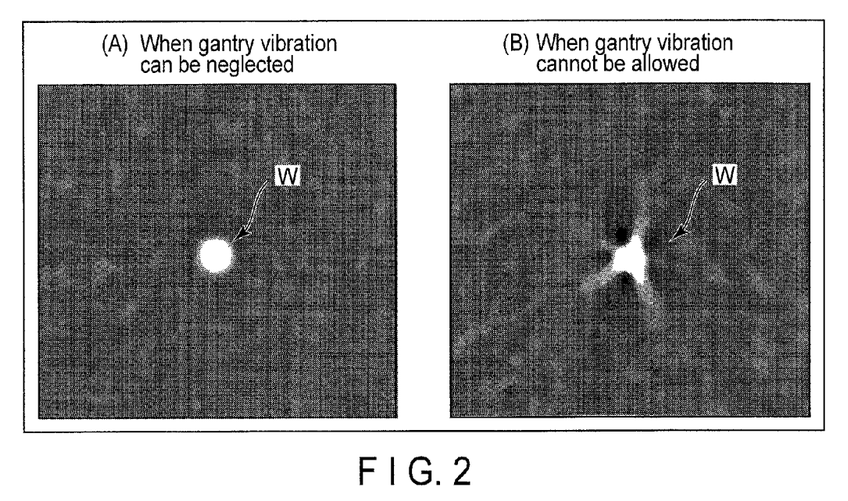
FIG. 2 is a view for explaining an artifact caused by gantry vibration.

In FIG. 2, (A) and (B) each indicate an example of the reconstructed image obtained by scanning a wire phantom (e.g., a copper wire of about 0.1 mm in diameter) which generates an impulse response and is placed in an FOV of the X-ray CT scanner 1 so as to be parallel to the rotation axis of the rotating portion 11. The high-luminance portion existing near the center in each of (A) and (B) in FIG. 2 is a tomographic image of the wire phantom (to be referred to as a wire phantom image W hereinafter).

In (A), the influence of the gantry vibration is small enough to be ignored, and the contour of the wire phantom image W forms an almost true circle. In contrast to this, in (B), the influence of the gantry vibration is too large to be allowed, and the contour of the wire phantom image W meanders and does not form a true circle. This artifact can be regarded as an error component which has occurred because of the negligence of a change in FCD (the distance from the focus to the rotation center), center channel value of the detector system 14, or the like due to gantry vibration at the time of reconstruction.

[Gantry Vibration Evaluation]

Figure 3:
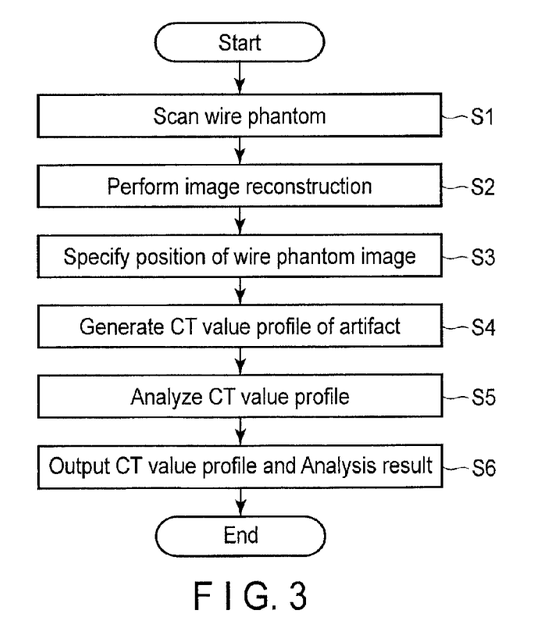
FIG. 3 is a flowchart for explaining operation in the first embodiment.

The X-ray CT scanner 1 according to this embodiment has a function of executing the processing procedure indicated by the flowchart of FIG. 3 to evaluate the degree of gantry vibration which becomes the cause of an artifact like that described above. The scanner starts this processing in response to an instruction to execute the processing which is issued when the user activates the maintenance mode by operating the input unit 24.

When starting this processing, the user sets a predetermined phantom on the bed 12 in advance. Assume that in this embodiment, the above wire phantom is used as this phantom. In addition, the wire phantom is set at a position slightly shifted from the rotation center of the rotating portion 11 (e.g., a position shifted from the rotation center by about 50 mm) so as to be parallel to the rotation axis of the rotating portion 11. The purpose of setting the wire phantom at a position shifted from the rotation center is to execute the processing to be described later upon eliminating the influence of an artifact irrelevant to the vibration of the gantry apparatus A which occurs near the rotation center.

When processing starts while the wire phantom is set in this state, the host controller 21 controls the gantry bed driving unit 17 to rotate the rotating portion 11, and applies a voltage to the X-ray tube 13 via the power supply unit 18 and the high voltage generation unit 19 to generate X-rays, thereby scanning the wire phantom (step S1). The raw data detected by the detector system 14 at this time is sent to the preprocessing unit 20 via the data acquisition circuit 15, the data transmission unit 16, and the like. The storage unit 23 stores the projection data generated after various types of correction in the preprocessing unit 20.

Subsequently, the reconstruction unit 22 generates reconstruction image data by a predetermined reconstruction technique using the projection data stored in the storage unit 23, and the storage unit 23 stores the generated data (step S2).

The extraction unit 251, the analysis unit 252, and the output unit 253 then start processing.

That is, first of all, the extraction unit 251 specifies the position of the wire phantom image W contained in the reconstruction image data stored in the storage unit 23 in step S2 (step S3). In this processing, for example, setting information indicating the position of the wire phantom image W is stored in the image processing unit 25 in advance, and the barycentric position of the wire phantom image W contained in the reconstruction image data is specified by using the setting information. In this case, when performing the processing in steps S1 and S2, the wire phantom needs to be set at the position indicated by the setting information.

As another method of specifying the position of the wire phantom image W, for example, it is possible to use a method of automatically specifying the position of the wire phantom image W by using, for example, the CT value (pixel value) of each pixel contained in reconstruction image data. In this method, a position corresponding to the highest CT value in reconstruction image data may be regarded as the barycentric position of the wire phantom image W.

Upon specifying the position of the wire phantom image W, the extraction unit 251 extracts the CT values of pixels existing on a locus surrounding the wire phantom image W contained in the reconstruction image data, and generates the CT value profile of an artifact (step S4).

Figure 4:
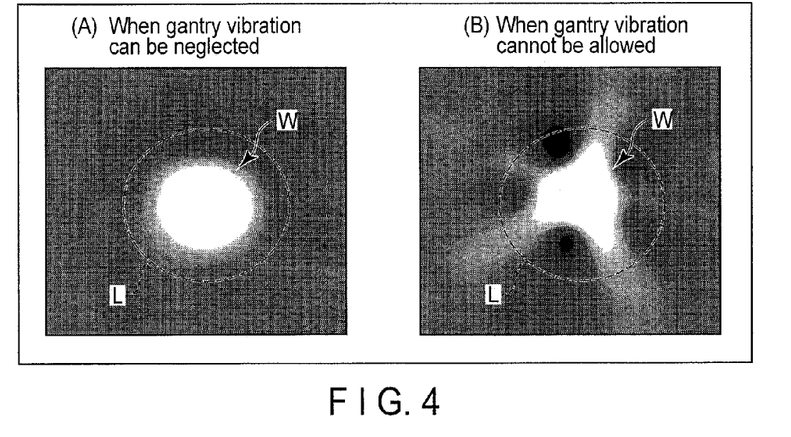
FIG. 4 is a view for explaining a CT value profile in the same embodiment.

A CT value profile in this embodiment will be concretely described. FIG. 4 shows enlarged views of the wire phantom images W contained in the images (A) and (B) shown in FIG. 2. In the embodiment, the extraction unit 251 extracts the CT values of pixels existing on a locus L surrounding the wire phantom image W from the reconstruction image data and arranges them along the circumferential direction of the locus L (radian direction), thereby generating the CT value profile of the artifact. Note that the locus L is a true circle centered at the barycentric position set in step S3. The diameter (or the radius) of the locus L may be stored in a memory in the image processing unit 25 in advance. Alternatively, the locus L may be automatically set by using, for example, the CT values of the respective pixels contained in the reconstruction image data so as to surround the wire phantom image W.

Figure 5:
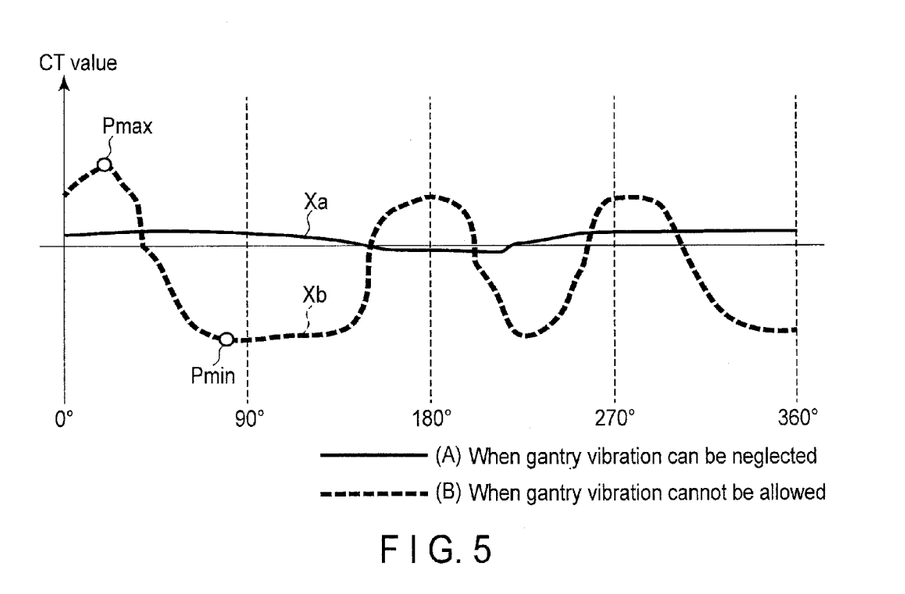
FIG. 5 is a view showing an example of a CT value profile generated in the same embodiment.

The CT value profile generated by this technique exhibits changes like those shown in FIG. 5. FIG. 5 shows two patterns of CT value profiles (a solid line Xa and a broken line Xb) in a graph form with the abscissa representing angles (0° to 360°) and the ordinate representing CT values.

The solid line Xa exhibits a small change in CT value as a whole with a long change period. In such a case, the influence of gantry vibration is estimated to be small enough to be negligible, as in the case of the image (A) in FIG. 2.

The broken line Xb exhibits a larger change in CT value than the solid line Xa, with a short change period. In such a case, the influence of gantry vibration is estimated to be too large to be allowed, as in the case of the image (B) in FIG. 2.

After the generation of the CT value profile in step S4, the analysis unit 252 performs various kinds of analyses using the profile (step S5). In this embodiment, in particular, the analysis unit 252 generates the frequency spectrum of the CT value profile generated in step S3. The analysis unit 252 may generate this frequency spectrum by using a known technique such as FFT (Fast Fourier Transform) in consideration of the rotational speed (e.g., about 0.35 sec) of the rotating portion 11.

Figure 6:
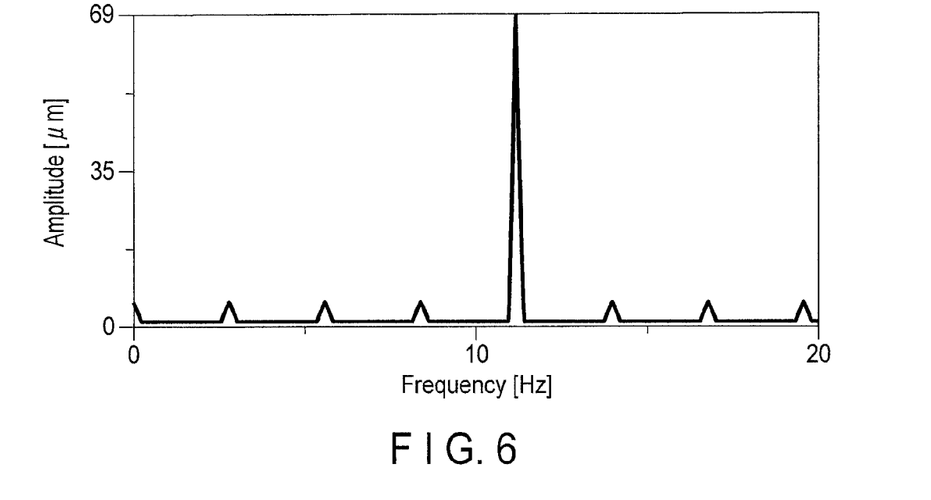
FIG. 6 is a graph showing an example of a frequency spectrum generated in the same embodiment.

FIG. 6 shows an example of the frequency spectrum generated by the analysis unit 252. FIG. 6 shows a frequency spectrum in a graph form with the abscissa representing the frequency and the ordinate representing the amplitude. According to this frequency spectrum, the amplitude greatly increases near 11 Hz. Based on such a frequency spectrum, the profiled artifact is estimated to have a natural frequency of about 11 Hz.

After the analysis of the CT value profile, the output unit 253 displays/outputs the CT value profile and a frequency spectrum as an analysis result to the display unit 26 (step S6). Note that the output unit 253 may also display/output an analysis result other than the frequency spectrum, e.g., the natural frequency of the artifact specified from the spectrum, to the display unit 26. It is also possible to print the CT value profile and the analysis result using a printer (not shown) or output them to a device connected via a communication unit by data transmission. In addition, the CT value profile and the analysis result may be output in a graph form shown in FIGS. 5 and 6 or may be output in another graph form or as numerical values contained in the CT value profile and the analysis result.

With the above operation, the scanner terminates the series of processing shown in the flowchart of FIG. 3.

The person who maintains the X-ray CT scanner 1 can quantitatively grasp the degree of the artifact caused around the wire phantom image W in the reconstructed image and easily determine the presence/absence of the influence of gantry vibration on the reconstructed image by referring to the CT value profiled displayed on the display unit 26 in this manner.

In addition, the displayed CT value profile or frequency spectrum serves as an effective clue for specifying the cause of gantry vibration. In addition, since a CT value profile and a frequency spectrum are displayed in a graph form, it is visually easy to grasp the state of the vibration of an artifact and a natural frequency.

The maintenance person may determine that the influence of gantry vibration on image quality cannot be neglected, when, for example, the CT value profile has a certain amplitude, and take necessary measures against a faulty portion of the gantry apparatus A which is empirically estimated from the natural frequency specified by the frequency spectrum.

Second Embodiment

The second embodiment will be described next.

This embodiment differs from the first embodiment in that it automatically determines on the X-ray CT scanner 1 side, based on the CT value profile described in the first embodiment, whether the influence of gantry vibration on image quality falls within an allowable range.

Figure 7:
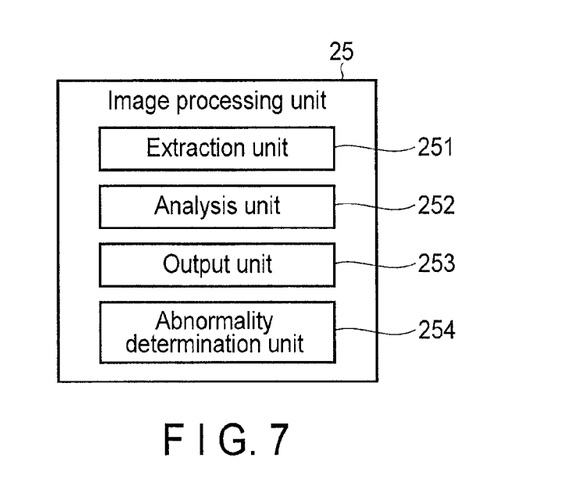
FIG. 7 is a block diagram showing the arrangement of an image processing unit in the second embodiment.

The arrangement of the X-ray CT scanner 1 in this embodiment is basically the same as that shown in FIG. 1. As shown in FIG. 7, however, an image processing unit 25 in this embodiment includes an abnormality determination unit 254 in addition to an extraction unit 251, an analysis unit 252, and an output unit 253. Like the units 251 to 253, the abnormality determination unit 254 is implemented by causing a processor to execute a computer program stored in a predetermined memory.

Figure 8:
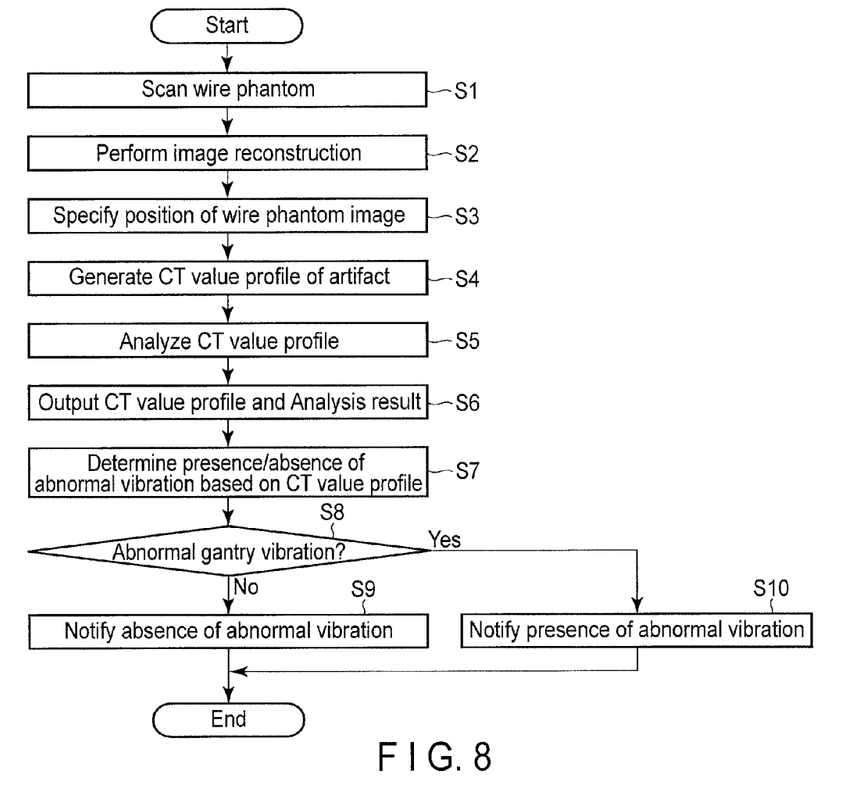
FIG. 8 is a flowchart for explaining operation in the same embodiment.

In a maintenance mode in this embodiment, the scanner executes the processing procedure indicated by the flowchart of FIG. 8 instead of the processing procedure indicated by the flowchart of FIG. 3. That is, as in the first embodiment, a host controller 21 scans a wire phantom (step S1). A reconstruction unit 22 generates reconstruction image data (step S2). The extraction unit 251 specifies the position of a wire phantom image W contained in the reconstruction image data (step S3), and generates the CT value profile of an artifact existing around the wire phantom image W contained in the reconstruction image data (step S4). The analysis unit 252 performs various kinds of analyses (step S5). The output unit 253 outputs the CT value profile and the analysis result to a display unit 26 (step S6).

Subsequently, the abnormality determination unit 254 determines whether abnormal vibration has occurred in a gantry apparatus A (step S7). In this processing, the abnormality determination unit 254 obtains, for example, a difference $\Delta CT$ (=|CTmax−CTmin|) between a maximum value CTmax and a minimum value CTmin of the CT values contained in the CT value profile generated in step S4. If the difference $\Delta CT$ is equal to or more than a predetermined threshold CTx ($\Delta CT \geq CTx$), the abnormality determination unit 254 determines that there is abnormal vibration. If the difference $\Delta CT$ is less than the threshold CTx ($\Delta CT < CTx$), the abnormality determination unit 254 determines that there is no abnormal vibration.

In addition, it is possible to determine the presence/absence of abnormal vibration based on a frequency F of vibration between 0° and 360° of a CT value profile. That is, when the frequency F is sufficiently high or low, an artifact associated with the profile becomes less noticeable in the reconstructed image. In consideration of this, the abnormality determination unit 254 determines the absence of abnormal vibration if the frequency F is equal to or more than a lower limit value Fmin and equal to or less than an upper limit value Fmax (Fmin≤F≤Fmax), and determines the presence of abnormal vibration if the frequency F is less than the lower limit value Fmin or exceeds the upper limit value Fmax (Fmin<F, <Fmax).

Furthermore, it is possible to combine these two determination methods. That is, the abnormality determination unit 254 determines the presence of abnormal vibration if the difference $\Delta C$ is equal to or more than the threshold CTx and the frequency F is less than the lower limit value Fmin ($\Delta CT \geq CTx$, F<Fmin), and the difference $\Delta C$ is equal to or more than the threshold CTx and the frequency F exceeds the upper limit value Fmax ($\Delta CT \geq CTx$, F>Fmax).

Note that the above threshold CTx, the lower limit value Fmin, and the upper limit value Fmax may be experimentally, empirically, or logically determined such that they become values that separate the allowable degree of influence on a reconstructed image from the unallowable degree of influence.

If the abnormality determination unit 254 determines the absence of abnormal vibration (NO in step S8) as a result of determination by the above technique, the output unit 253 displays, on the display unit 26, a message stating that no abnormal vibration has occurred (step S9). If the abnormality determination unit 254 determines the presence of abnormal vibration in step S7 (YES in step S8), the output unit 253 displays, on the display unit 26, a message stating that abnormal vibration has occurred (step S10). Note however that in steps S9 and S10, the determination result may be notified by printing by a printer (not shown), data transmission to a connected device via a communication unit, speech output from a loudspeaker (not shown), or the like.

After step S9 or S10, the scanner terminates the series of processing indicated by the flowchart of FIG. 8.

In this manner, this embodiment automatically determines whether abnormal vibration has occurred in the gantry apparatus A, and notifies the result. This makes it unnecessary for the maintenance person to determine the presence/absence of abnormal vibration, and hence saves him/her from having to perform operation necessary for the determination.

In addition, obviously, this embodiment has the same effects as those of the first embodiment.

Third Embodiment

The third embodiment will be described next.

This embodiment differs from the second embodiment in that when determining, as a result of the determination of the presence/absence of abnormal vibration described in the second embodiment, that abnormal vibration has occurred, an X-ray CT scanner 1 notifies a matter suspected to be the cause of abnormal vibration.

Figure 9:
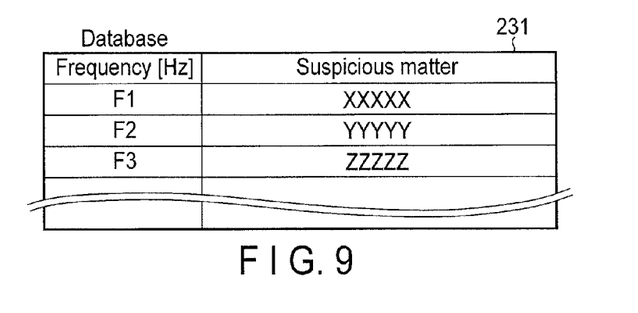
FIG. 9 is a view showing the arrangement of a database in the third embodiment.

The arrangement of the X-ray CT scanner 1 according to this embodiment is basically the same as that of the second embodiment. A storage unit 23 stores a database 231 having the arrangement shown in FIG. 9. The database 231 is configured to make matters suspected to be the causes of artifacts (suspicious matters) correspond to the natural frequencies of the respective artifacts. The respective frequencies and the corresponding suspicious matters are the empirically obtained results registered in the database 231.

Figure 10:
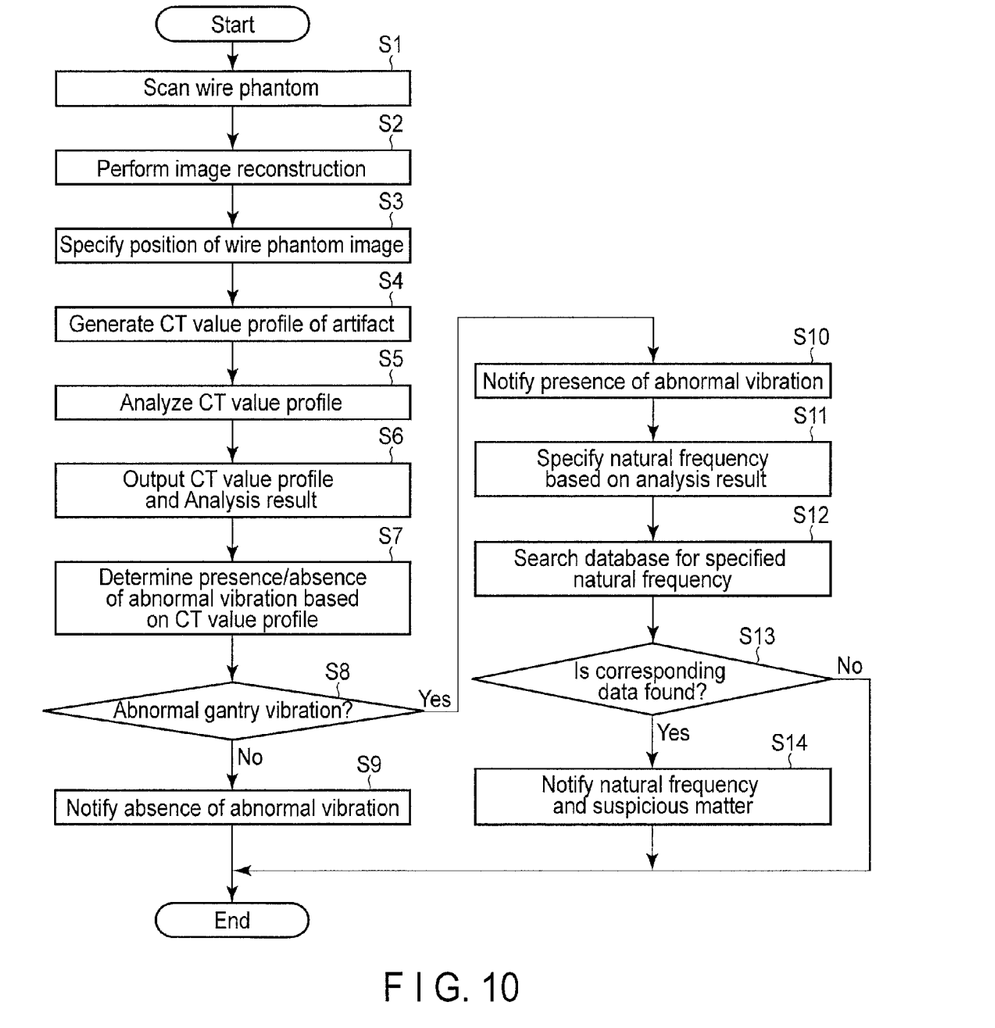
FIG. 10 is a flowchart for explaining operation in the same embodiment.

In the maintenance mode in this embodiment, the scanner executes the processing procedure indicated by the flowchart of FIG. 10 instead of the processing procedure indicated by the flowchart of FIG. 8. First of all, as in the second embodiment, a host controller 21 scans a wire phantom (step S1). A reconstruction unit 22 generates reconstruction image data (step S2). An extraction unit 251 specifies the position of a wire phantom image W contained in the reconstruction image data (step S3), and generates the CT value profile of an artifact existing around the wire phantom image W (step S4). An analysis unit 252 performs various kinds of analyses by using the profile (step S5). An output unit 253 displays/outputs the CT value profile and the analysis result to a display unit 26 (step S6). Thereafter, an abnormality determination unit 254 determines the presence/absence of abnormal vibration (step S7). If the abnormality determination unit 254 determines the absence of abnormal vibration (NO in step S8), the output unit 253 displays/outputs, to the output unit 253, a message stating that no abnormal vibration has occurred (step S9).

If the abnormality determination unit 254 determines the presence of abnormal vibration (YES in step S8), the output unit 253 displays/outputs a message stating that abnormal vibration has occurred (step S10). In addition, in this case, the analysis unit 252 specifies a natural frequency Fx of an artifact based on the frequency spectrum generated in step S5 (step S11). In this processing, the analysis unit 252 may specify a frequency at which the amplitude greatly increases relative to the surrounding amplitudes as shown in, for example, FIG. 6, and regard the frequency as the natural frequency Fx of the artifact.

Upon specifying the natural frequency Fx of the artifact, the analysis unit 252 searches for a frequency approximate to the natural frequency Fx from the database 231 (step S12). In this processing, it is possible to regard, as frequencies approximate to natural frequency Fx, for example, frequencies existing in the range defined by the lower limit value obtained by subtracting a predetermined error $\epsilon$ from the natural frequency Fx and the upper limit value obtained by adding the error $\epsilon$ to the natural frequency Fx.

If a frequency approximate to the natural frequency Fx is found from the database 231 as a result of this search (YES in step S13), a suspicious matter associated with the frequency found by the output unit 253 is read out from the database 231 and is displayed, together with the natural frequency Fx, on the display unit 26 (step S14).

If no frequency approximate to the natural frequency Fx is found from the database 231 (NO in step S13) after step S9 or S14 or in step S12, the scanner terminates the series of processing indicated by the flowchart of FIG. 10.

As described above, this embodiment is configured to automatically display/output a suspicious matter as the cause of abnormal vibration to the display unit 26. This arrangement makes it very easy to specify the cause of abnormal vibration, and hence makes maintenance operation for handling abnormal vibration much more efficient.

In addition, obviously, this embodiment has the same effects as those of the first and second embodiments.
(Modification)

Note that the arrangements disclosed in the respective embodiments can be embodied in the execution stage by modifying the respective constituent elements as needed. For example, the following are specific modifications.

(1) In each embodiment described above, the image processing unit 25 in the X-ray CT scanner 1 implements the extraction unit 251, the analysis unit 252, the output unit 253, the abnormality determination unit 254, and the like, and the units 251 to 254 perform the processing in steps S3 to S14. However, an image processing apparatus different from the X-ray CT scanner 1 may execute the processing in steps S3 to S14. In this case, as the above image processing apparatus, it is possible to use various types of apparatuses such as a personal computer, a server connected to a network in a hospital, or a dedicated computer system configured to execute the processing in steps S3 to S14. In addition, reconstruction image data to be processed by such an image processing apparatus may be read out from a storage unit in the X-ray CT scanner 1, a storage unit provided in the image processing apparatus, or a recording medium such as a CD-ROM or USB memory.

(2) Each embodiment described above uses a wire phantom as an object, and executes the processing shown in FIGS. 3, 8, and 10. However, a phantom other than a wire phantom may be used. In addition, when a phantom having a section with a shape other than a circular shape is to be used, the arrangement disclosed in each embodiment described above may be modified as needed. For example, the locus L may be deformed in accordance with the shape of the phantom.

(3) In each embodiment described above, the processor executes computer programs stored in a memory to implement the extraction unit 251, the analysis unit 252, the output unit 253, and the abnormality determination unit 254. However, each embodiment is not limited to this. It is possible to download the above computer programs from a predetermined network to the X-ray CT scanner 1 or the image processing apparatus described in (1). Alternatively, information for implementing the same functions as those described above which is stored in a recording medium may be installed in the X-ray CT scanner 1 or the above image processing apparatus. As a recording medium, a CD-ROM, a USB memory, or the like can be used. In addition, a recording medium in any form can be used as long as it is readable for a device connected to the X-ray CT scanner 1 or the image processing apparatus. Alternatively, functions obtained in advance by installing or downloading information may be implemented in cooperation with the OS (Operating System) and the like in the X-ray CT scanner 1 or the image processing apparatus.

Some embodiments of the present invention have been described above. However, these embodiments are presented merely as examples and are not intended to restrict the scope of the invention. These novel embodiments can be carried out in various other forms, and various omissions, replacements, and alterations can be made without departing from the gist of the invention. The embodiments and their modifications are also incorporated in the scope and the gist of the invention as well as in the invention described in the claims and their equivalents.

What is claimed is:

1. An X-ray CT scanner, comprising:
a gantry unit including an X-ray source configured to irradiate an object with X-rays and an X-ray detector configured to detect X-rays transmitted through the object, and configured to rotate the X-ray source and the X-ray detector while placing the X-ray source and the X-ray detector so as to make the X-ray source and the X-ray detector face each other;
a reconstruction unit configured to generate reconstruction image data by using data acquired by the X-ray detector;
an extraction unit configured to extract, when using a predetermined phantom as the object, pixel values of pixels existing on a locus surrounding a tomographic image of the phantom contained in reconstruction image data generated by the reconstruction unit based on data acquired by the X-ray detector, wherein the locus has a circular shape surrounding the tomographic image of the phantom; and
an output unit configured to output an extraction result obtained by the extraction unit or information obtained based on the extraction result, wherein the output unit is configured to output a graph obtained by plotting pixel values, which are extracted by the extraction unit along a circumferential direction of the locus, as a function of angle.

2. The X-ray CT scanner of claim 1, further comprising an analysis unit configured to generate a frequency spectrum of an artifact existing on the locus by analyzing an extraction result obtained by the extraction unit,
wherein the output unit outputs a frequency spectrum generated by the analysis unit or a natural frequency of the artifact specified from the frequency spectrum.

3. The X-ray CT scanner of claim 1, further comprising an abnormality determination unit configured to determine whether abnormal vibration has occurred in the gantry unit, based on an extraction result obtained by the extraction unit, wherein the output unit outputs a determination result obtained by the abnormality determination unit.

4. The X-ray CT scanner of claim 3, wherein the abnormality determination unit determines that abnormal vibration has occurred, if a difference between a maximum value and a minimum value of pixel values extracted by the extraction unit exceeds a predetermined threshold, and determines that abnormal vibration has not occurred, if the difference is less than the threshold.

5. The X-ray CT scanner of claim 1, further comprising:
a database configured to register an event suspected as a cause of an artifact appearing in the reconstruction image data generated by the reconstruction unit, in association with a natural frequency of the artifact; and
an analysis unit configured to specify a natural frequency of an artifact existing on the locus by analyzing an extraction result obtained by the extraction unit,
wherein the output unit outputs a cause of an artifact registered in the database, in association with a natural frequency specified by the analysis unit.

6. The X-ray CT scanner of claim 5, further comprising an abnormality determination unit configured to determine whether abnormal vibration has occurred in the gantry unit, based on an extraction result obtained by the extraction unit,
wherein the output unit outputs the cause of the artifact when the abnormality determination unit determines that abnormal vibration has occurred, and does not output a cause of the artifact when the abnormality determination unit determines that no abnormal vibration has occurred.

7. An image processing apparatus, comprising:
a storage unit configured to store reconstruction image data including a tomographic image of a predetermined phantom which is generated by an X-ray CT scanner including a gantry unit which rotates an X-ray source configured to irradiate an object with X-rays and an X-ray detector configured to detect X-rays transmitted through the object while placing the X-ray source and the X-ray detector so as to make the X-ray source and the X-ray detector face each other;
an extraction unit configured to extract pixel values of pixels existing on a locus surrounding a tomographic image of the phantom contained in reconstruction image data stored in the storage unit, wherein the locus has a circular shape surrounding the tomographic image of the phantom; and
an output unit configured to output an extraction result obtained by the extraction unit or information obtained based on the extraction result, wherein the output unit is configured to output a graph obtained by plotting pixel values, which are extracted by the extraction unit along a circumferential direction of the locus, as a function of angle.

8. The image processing apparatus of claim 7, further comprising an abnormality determination unit configured to determine whether abnormal vibration has occurred in the gantry unit of an X-ray CT scanner used to generate the reconstruction image data, based on an extraction result obtained by the extraction unit,
wherein the output unit outputs a determination result obtained by the abnormality determination unit.

9. The image processing apparatus of claim 7, further comprising:
a database configured to register an event suspected as a cause of an artifact appearing in the reconstruction image data in associated with a natural frequency of the artifact; and
an analysis unit configured to specify a natural frequency of an artifact existing on the locus by analyzing an extraction result obtained by the extraction unit,
wherein the output unit outputs a cause of an artifact registered in the database in association with a natural frequency specified by the analysis unit.

* * * * *